(12) United States Patent
Guerin et al.

(10) Patent No.: US 6,395,230 B1
(45) Date of Patent: May 28, 2002

(54) PELLISTOR

(75) Inventors: Samuel Guerin, Cerelles (FR); Philip Nigel Bartlett, Hampshire (GB)

(73) Assignee: City Technology Limited, Portsmouth (GB)

( * ) Notice: Subject to any disclaimer, the term of this patent is extended or adjusted under 35 U.S.C. 154(b) by 0 days.

(21) Appl. No.: 09/762,690

(22) PCT Filed: Aug. 11, 1999

(86) PCT No.: PCT/GB99/02644

§ 371 (c)(1),
(2), (4) Date: Mar. 26, 2001

(87) PCT Pub. No.: WO00/14307

PCT Pub. Date: Mar. 16, 2000

(30) Foreign Application Priority Data

Sep. 2, 1998 (GB) ............................................. 9819160

(51) Int. Cl.$^7$ ............................................. G01N 30/96
(52) U.S. Cl. .............................. 422/88; 422/94; 422/98
(58) Field of Search .......................... 422/88, 94, 174, 422/95, 98; 436/17, 141; 438/54, 680, 613; 423/328, 705

(56) References Cited

U.S. PATENT DOCUMENTS

| | | | | |
|---|---|---|---|---|
| 4,070,207 A | * | 1/1978 | Holdman | 148/553 |
| 4,977,038 A | * | 12/1990 | Sieradzki et al. | 428/610 |
| 4,983,217 A | * | 1/1991 | Lopez Quintela et al. | 75/739 |
| 5,549,871 A | | 8/1996 | Kocache et al. | |
| 5,718,878 A | * | 2/1998 | Zhang | 423/610 |
| 5,837,639 A | * | 11/1998 | Kresge et al. | 502/64 |
| 5,855,864 A | * | 1/1999 | Pinnavaia et al. | 423/708 |
| 5,902,556 A | * | 5/1999 | Van De Vyver et al. | 422/174 |
| 5,958,367 A | * | 9/1999 | Ying et al. | 423/701 |
| 6,054,111 A | * | 4/2000 | Antonietti et al. | 423/702 |
| 6,056,545 A | * | 5/2000 | Lemchen | 433/20 |
| 6,203,925 B1 | * | 3/2001 | Attard et al. | 428/613 |

OTHER PUBLICATIONS

Attard, "Mesoporous platinum films from Iyotropic liquid crystalline phases" Science, vol. 278, Oct. 31, 1997, p. 838–840 XP002101941) cited in application.

* cited by examiner

*Primary Examiner*—Jeffrey Snay
*Assistant Examiner*—Samuel P Siefke
(74) *Attorney, Agent, or Firm*—Robert F. I. Conte; Lee, Mann, Smith, McWilliams, Sweeney & Ohlson (57) ABSTRACT

A method of manufacturing a pellistor comprises providing a porous catalyst layer (11) on a heater by electrodepositing material from a mixture containing the catalyst and a structure-directing agent in an amount sufficient to form an homogenous lyotropic liquid crystalline phase in the mixture.

14 Claims, 8 Drawing Sheets

PELLISTOR

The method relates to a method of manufacturing a pellistor.

Pellistors are catalytic oxidation sensors which measure concentrations of combustible gases in air up to the lower explosive limit. The sensors are matched in pairs of elements, each conventionally comprising a platinum wire coil embedded within a catalytic bead. An active detector element oxidises combustible gases, while an inert reference element, named the compensator, compensates for changes in ambient conditions. The coil serves two purposes. Firstly, in the detector and compensator it is used to heat the bead electrically to its operating temperature (about 500° C.); and secondly, for the detector, it is also used to detect changes in temperature produced by the oxidation of the flammable gas.

A Wheatstone Bridge circuit is used to measure the concentration of combustible gas in air. The Bridge is balanced by a variable resistance, with both elements at their operating temperature; an out-of-balance signal is produced when a combustible gas is detected. The signal is proportional to the concentration of combustible gas.

More recently, attempts have been made to manufacture planar pellistor arrangements in which the conventional coil is replaced by a planar electrode on an inert substrate such as silicon. Typically, the silicon is micro machined to provide a thin membrane on which the heater is deposited. This is described in "Microsensors, Principles and Applications", Julian W. Gardner, pages 242–243, published by John Wiley & Sons. Potentially, planar arrangements could provide a number of important benefits. These are as follows:

Lower power: Conventional coil pellistors can only be produced with power consumption down to about 100 mW per element (i.e. 200 mW per pair). The platinum wire diameter to wind coils for these power levels is about 10 $\mu$m. This is the practical lower limit at which it is possible to work, due to a combination of visibility and other handling difficulties. Micro machining is capable of fabrication down to much smaller dimensions and device powers of between $\frac{1}{3}$ to $\frac{2}{3}$ those of conventional devices have been achieved (e.g. a device manufactured by Microsens S.A. has a specification of 60 mW (25 mA at 2.4 volts) for a detector/compensator pair). The ability to integrate two or more elements (i.e. a detector/compensator pair) in very close proximity can also provide economies in power consumption.

Volume production: Conventional coil pellistor manufacture is an inherently labour intensive operation and is fundamentally not amenable to scale up for volume production. Micro machining, by its very nature, is a volume production method of fabrication and less suited to small-scale operation due to the high capital investment required. Depending on the exact technique employed, however, there are numerous contractors able to undertake production runs of different sizes. In principle, micro machined devices could be manufactured more consistently and cost effectively than conventional devices for a volume market. Even for relatively low volume industrial markets there would be a manufacturing advantage to the micro machined products which could produce more consistent quality devices with an automated method of fabrication and might offset any increased production cost associated with relatively small batch sizes.

Improved sensitivity: Conventional coil technology limits the type of material which can be employed due to the mechanical requirements placed upon the wire. In micro machined devices, it is common to employ encapsulated heaters, hence allowing the possibility of employing materials with more favourable properties. For example, metals or alloys with higher temperature coefficients of resistance than the normally employed Pt may offer improved resolution.

Pellistors have so far found applications in industrial areas to provide a warning of combustible gas accumulation to explosive levels, e.g. oil rigs, mines, sewers and other confined spaces. These markets are relatively small and suited to conventional pellistors. Other markets exist for lower cost devices, such as domestic applications which have so far been addressed by semiconductor devices. However, these suffer from well known shortcomings in performance, which severely limit their applicability.

The catalytic coatings produced on planar devices have usually been laid down onto the micro mechanical heater substrates with coating methods (such as vapour deposition or sputtering) which result in a relatively low surface area catalyst layer. This tends to produce devices whose catalytic activity is inherently poor and which have comparatively short operational lifetimes compared to conventional pellistors. This is particularly true when such devices are operated in environments containing materials which poison and/or inhibit the catalyst surface, e.g. silicone vapours, hydrogen sulphide. It is well known that the poison resistance in such devices is greatly enhanced by using high surface area catalysts which offer some redundancy of sites.

Attempts have been made to coat the micro machined planar heater substrates with conventional catalyst material mixes, but it is very difficult to do this accurately on areas with dimensions well below 1 mm, as is often required on micro machined devices. Furthermore, the micromachined heaters are unlikely to have sufficient mechanical strength to allow conventional methods (requiring contact with the substrate) to be employed, despite the fact that they may have excellent performance in response to thermal or mechanical shock. Additionally, the adhesion of the catalyst to the substrate is generally very poor. In extreme cases, the catalyst layer breaks away from the substrate resulting in total device failure, and/or heat transfer from the substrate to the catalyst is poor, resulting in higher power consumption to maintain the catalyst at its optimum operating temperature.

In accordance with the present invention, a method of manufacturing a pellistor comprises providing a porous catalyst layer on a heater by electrodepositing material from a mixture containing the catalyst and a structure-directing agent in an amount sufficient to form an homogenous lyotropic liquid crystalline phase in the mixture.

We have realised that it is possible to achieve very good porous catalyst layers having high surface areas using an electrodepositing technique. Although this is particularly suitable for use with planar pellistors and thus micro machined structures, the technique could also be applied to non-planar substrate geometries including conventional coil heaters.

We have found that the new catalyst layer can withstand the high temperatures associated with pellistor operation and is also durable and substantially poison resistant.

The process enables closely controlled porous catalyst layers to be laid down, if required in very small regions such as less than 100 $\mu$m$^2$, for example down to about 50 $\mu$m$^2$. Typical pore sizes are in the mesoporous range with internal diameters from 13 to 200 Angstroms, preferably 17 to 40 Angstroms.

It should be noted in particular that this method allows the amount and location of catalyst to be optimised in contrast to conventional pellistors where the bead is required to provide a support for the catalyst and introduces a significant heat sink thus requiring wasteful power input. The invention, in contrast, provides a substantially pure catalyst layer without any other material being present to act as a heat sink.

The material may be deposited onto the heater through a mask to provide even further control of the deposit area.

A particularly useful technique is described by Attard et al in "Mesoporous Platinum Films from Lyotropic Liquid Crystalline Phases", Science, Vol. 278, 31 Oct. 31, 1997, pages 838–840.

The structure-directing agent is included in the mixture in order to impart an homogeneous lyotropic liquid crystalline phase to the mixture. The liquid crystalline phase is thought to function as a structure-directing medium or template for film deposition. By controlling the nanostructure of the lyotropic liquid crystalline phase, and electrodepositing, a film may be synthesised having a corresponding nanostructure. For example, films deposited from normal topology hexagonal phases will have a system of pores disposed on an hexagonal lattice, whereas films deposited from normal topology cubic phases will have a system of pores disposed in cubic topology. Similarly, films having lamellar nanostructures may be deposited from lamellar phases.

Accordingly, by exploiting the rich lyotropic polymorphism exhibited by liquid crystalline phases, precise control over the structure of the films is achieved, enabling the synthesis of well-defined porous films having a long range spatially and orientationally periodic distribution of uniformly sized pores.

Any suitable amphiphilic organic compound or compounds capable of forming an homogeneous lyotropic liquid crystalline phase may be used as the structure-directing agent, either low molar mass or polymeric. These may include compounds sometimes referred to as organic directing agents. In order to provide the necessary homogeneous liquid crystalline phase, the amphiphilic compound will generally be used at a high concentration, typically at least about 10% by weight, preferably at least 20% by weight, and more preferably at least 30% by weight, based on the total weight of the solvent and amphiphilic compound.

Suitable compounds include organic surfactant compounds of the formula RQ wherein R represents a linear or branched alkyl, aryl, aralkyl or alkylaryl group having from 6 to about 60 carbon atoms, preferably from 12 to 18 carbon atoms, and Q represents a group selected from: $[O(CH_2)_m]_n)$ OH wherein m is an integer from 1 to about 4 and preferably m is 2, and n is an integer from 2 to about 60, preferably from 4 to 8; nitrogen bonded to at least one group selected from alkyl having at least four carbon atoms, aryl, aralkyl, and alkylaryl; and phosphorus or sulphur bonded to at least two oxygen atoms.

Other suitable structure-directing agents include monoglycerides, phospholipids and glycolipids.

Preferably, non-ionic surfactants such as octaethylene glycol monododecyl ether ($C_{12}EO_8$, wherein EO represents ethylene oxide) and octaethylene glycol monohexadecyl ether ($C_{16}EO_8$) are used as structure-directing agents.

Further details of preferred aspects of this method are described in WO 99/00536, the content of which is included herein by reference.

Any conventional catalyst can be used, typical examples including palladium, platinum, iridium and rhodium. In addition, mixtures of two or more of these could be used while one or more could be codeposited together with a support such as alumina or silica.

In the case of a planar electrode, this may be in a serpentine form in order to increase the length of the electrode within a predefined area.

The ability to localise the catalyst in the regions where the heater is known to be operating at maximum efficiency optimises the sensitivity obtained per unit power input.

In general, prior to the electrodepositing step, the method comprises providing an electrode on the heater structure which contacts the mixture during the electrodepositing process. This enables the region of deposit to be controlled and also separates the components. involved with the electrodepositing step from the heater structure. However, it may be possible in some circumstances to use the conductor forming the heater as one of the electrodes which is used during the electrodepositing step.

Some examples of pellistors according to the invention and methods for their manufacture will now be described with reference to the accompanying drawings in which.

Figure 1:
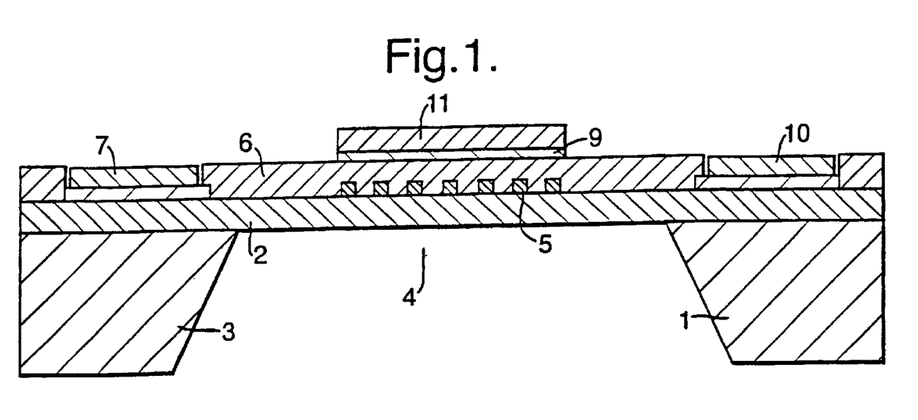
FIG. 1 is a schematic cross-section through a partially manufactured pellistor.
Figure 2:
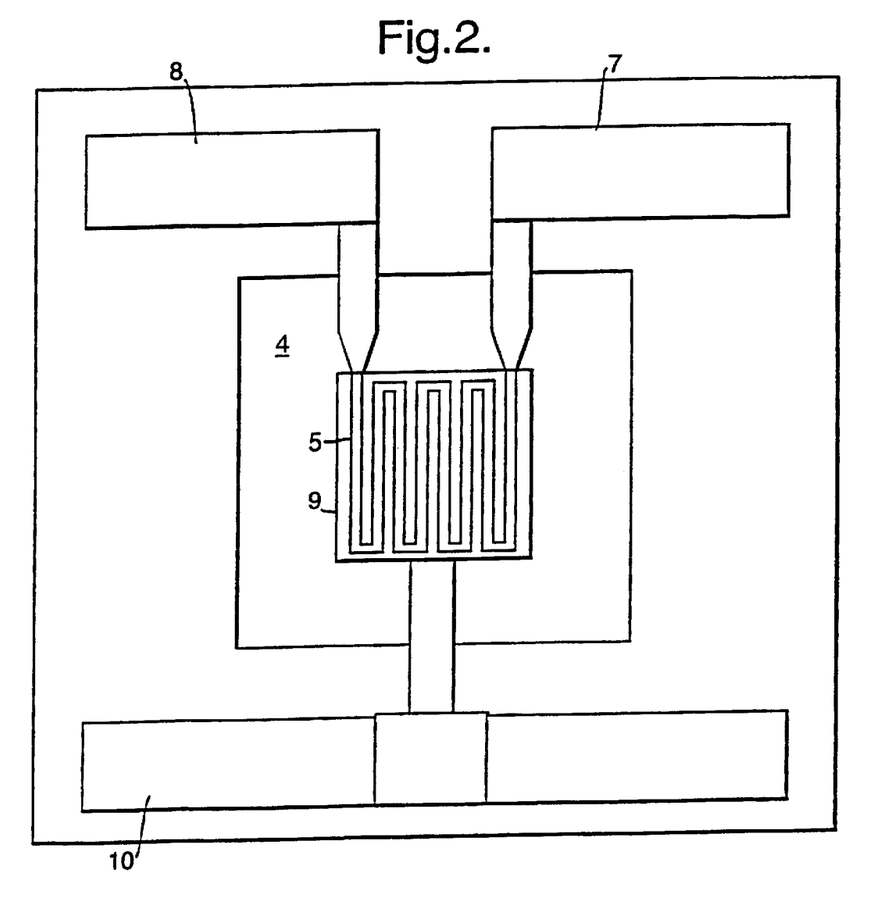
FIG. 2 is a plan of the pellistor shown in FIG. 1 prior to provision of the catalyst layer.

The partially manufactured pellistor illustrated in FIG. 1 comprises a silicon substrate 1 on which has been deposited a layer of silicon nitride 2 (or silicon oxynitride). A serpentine, platinum electrode 5 has been vacuum deposited onto the silicon nitride layer 2. A further silicon nitride layer 6 is then provided over the electrode 5 as an inert encapsulation. The overall thickness of this silicon nitride layer 6 is less than 1 micron, for example 0.3 microns. The ends of the electrode 5 are electrically coupled to a pair of contact pads 7,8 deposited on the substrate 1 as can be seen in FIG. 2. So far, the construction described is conventional.

In order for the device to function as a pellistor, it is necessary to provide a catalyst layer to promote combustion of the gas to be detected. To achieve this, a mask (not shown) defining the geometry and position of an electrode is provided on the layer 6 using standard photo lithographic techniques. A further electrode of gold 9 is then vacuum deposited through the mask onto part of the silicon nitride layer 6 overlying the turns of the electrode 5. The electrode 9 is coupled to a contact pad 10. One of the important aspects of this invention is the ability to localise the provision of the catalyst layer 11 and this is achieved by limiting the size of the electrode 9 since the catalyst layer will only deposit onto the electrode 9. The mask is then removed.

As an alternative to gold, platinum or palladium or highly doped amorphous silicon could be used.

At this stage the silicon substrate 1 is micromachined at 3 so that a thin membrane 4 of silicon nitride is defined having a thickness of about 0.3μ. The membrane has typical lateral dimensions of 2 mm×2 mm. The thin membrane reduces heat loss from the heater so that it has a low heat capacity leading to a very fast time constant and low power consumption.

A suitable catalyst/liquid crystal mixture is then prepared and this can be based on any of the examples described in the Attard et al paper mentioned above and in the preferred case the mixture is as follows:
pure deionized water
heptane
palladium salt: ammonium tetrachloropalladate
liquid crystal template: octaethylene glycol monohexadecyl ether, formulae can be:,
$C_{32}H_{66}O_9$ or $CH_3(CH_2)_{15}(OCH_2CH_2)_8OH$ from Fluka.
 the ratios used were: % (wt) template: 55% % (wt) water: 45%
 the ratio salt to water in weight was around 0.3
 the ratio of heptane was 4 moles of template to 1 mole of heptane.
This leads to the quantities listed below:
template: 400 mg
heptane: 16.9 mg
water: 327.3 mg
salt: 98.2 mg After weighing the template, the process involves adding the heptane, adding the water and then adding the palladium salt. The solution then needs to be mixed to make sure it is a homogeneous thick brownish paste. In a simple approach illustrated schematically in FIG. 3, the mixture is then fed into a pipette 20 so as to form a drop 21 into which extends a Pt counter electrode 22. A voltage is applied across the electrode 22 and the electrode 9 and as a result material 11 is deposited onto the electrode 9. The deposit comprises two interpenetrating phases of template and catalyst materials each with very well controlled, uniform high surface area structures. The template component can then be removed with acid or the like although it is thought that this is not always necessary.

Figure 3:
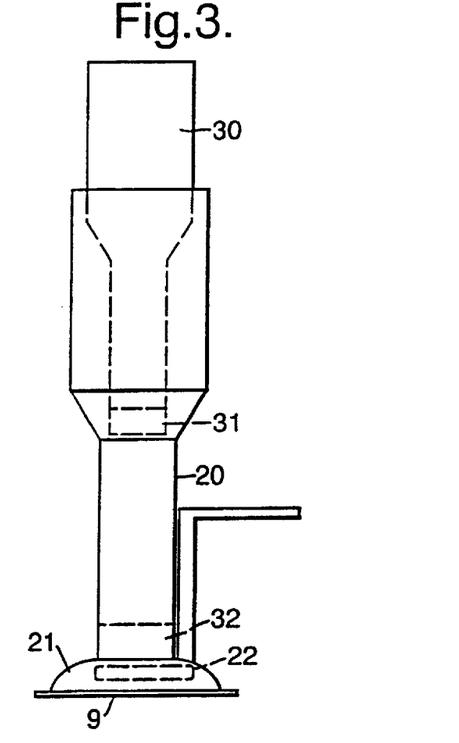
FIG. 3 is a schematic side view illustrating the provision of the catalyst layer.

In the preferred technique, an additional reference electrode 30 such as a Saturated Calomel Electrode (SCE) is used, the electrical "contact" between the three electrodes being made via glass frits 31,32. The additional use of the third (reference) electrode allows greater control of the potentials during the deposition and subsequent conditioning processes.

Deposition was always done at room temperature at 100 mV vs SCE. The amount of charge passed to make a working gas sensor is around 20 mC.

In some cases, the mixture could be deposited through a mask overlying the electrode 9. Irrespective of the size of the drop (beyond the minimum required to cover the gold electrode), the catalyst will still only grow on the electrode. However, depending on the nature of the peripheral construction (e.g. the strength of the wires connecting the heater to the packaging), it can be advantageous to limit the drop size using a mask.

The deposit was then washed in deionised water for one or two hours, and then cycled in 2M $H_2SO_4$ between 0.2V and 1.1V vs SCE until the charge passed in the stripping peak of the oxide reaches a maximum.

Figure 4:
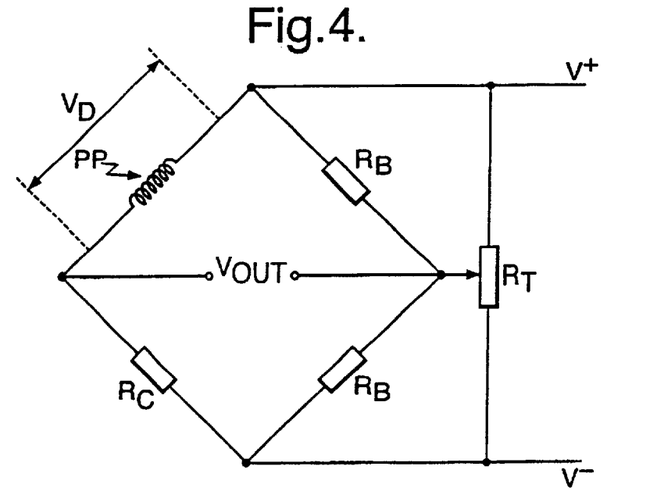
FIG. 4 illustrates a Wheatstone bridge circuit used to test the performance of the pellistor.

Experiments have been carried out on some pellistors constructed in accordance with the invention using a Wheatstone bridge circuit of the form shown in FIG. 4. In this diagram, PP is the pellistor under test, $R_c$ has a resistance of about 300Ω, $R_8$ has a resistance of about 100Ω, $R_T$ has a resistance of about 1KΩ, the total supply voltage $V^+$–$V^-$ is about 14.2 volts with a total bridge current of about 120 mA. The current passing through the pellistor is about 30 mA.

The circuit differs from that which will be used in operation since no compensator is used. However, in the absence of a compensator, this would be expected to reduce the overall performance, of the system, particularly in terms of signal stability. The resistance values in the balancing arm of the bridge have not been optimised to minimise overall power consumption in the initial experiments. It is nevertheless possible to estimate the power consumed by a single micromachined element, since the total bridge current is known, as is the voltage across the active device. This gives a value of about 165 mW for operation @ 5.5V. Under these conditions the device heater resistance is about 300Ω.

The devices tested were not placed in diffusion limiting cans or the like although such a can might be used in practice.

Figure 5:
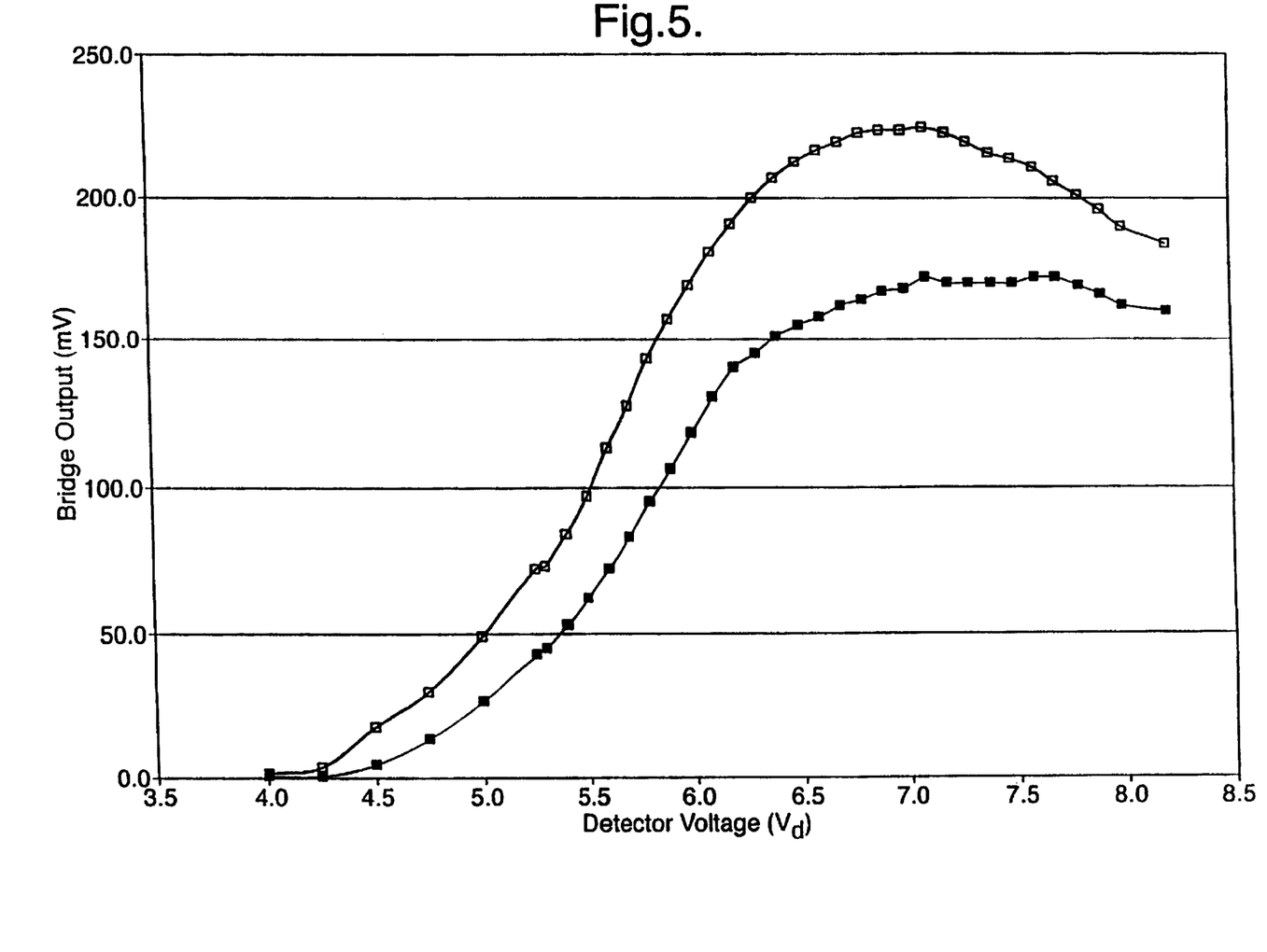
FIG. 5 illustrates graphically the change in bridge output (corrected for baseline shift with detector voltage) against detector voltage in response to 2.5% methane for two different pellistors.

FIG. 5 shows the response of two prototype mesoporous Pd devices to 2.5% methane in air as a function of the operating voltage across the sensor. Although the optimum sensitivity is obtained at about 7.0V, all subsequent data discussed below was actually obtained by operating at only 5.5V in order to reduce the thermal stress on the substrates. Thus, the results quoted do not represent the optimum performance which might eventually be envisaged, albeit at the expense of increased power consumption.

Figure 6:
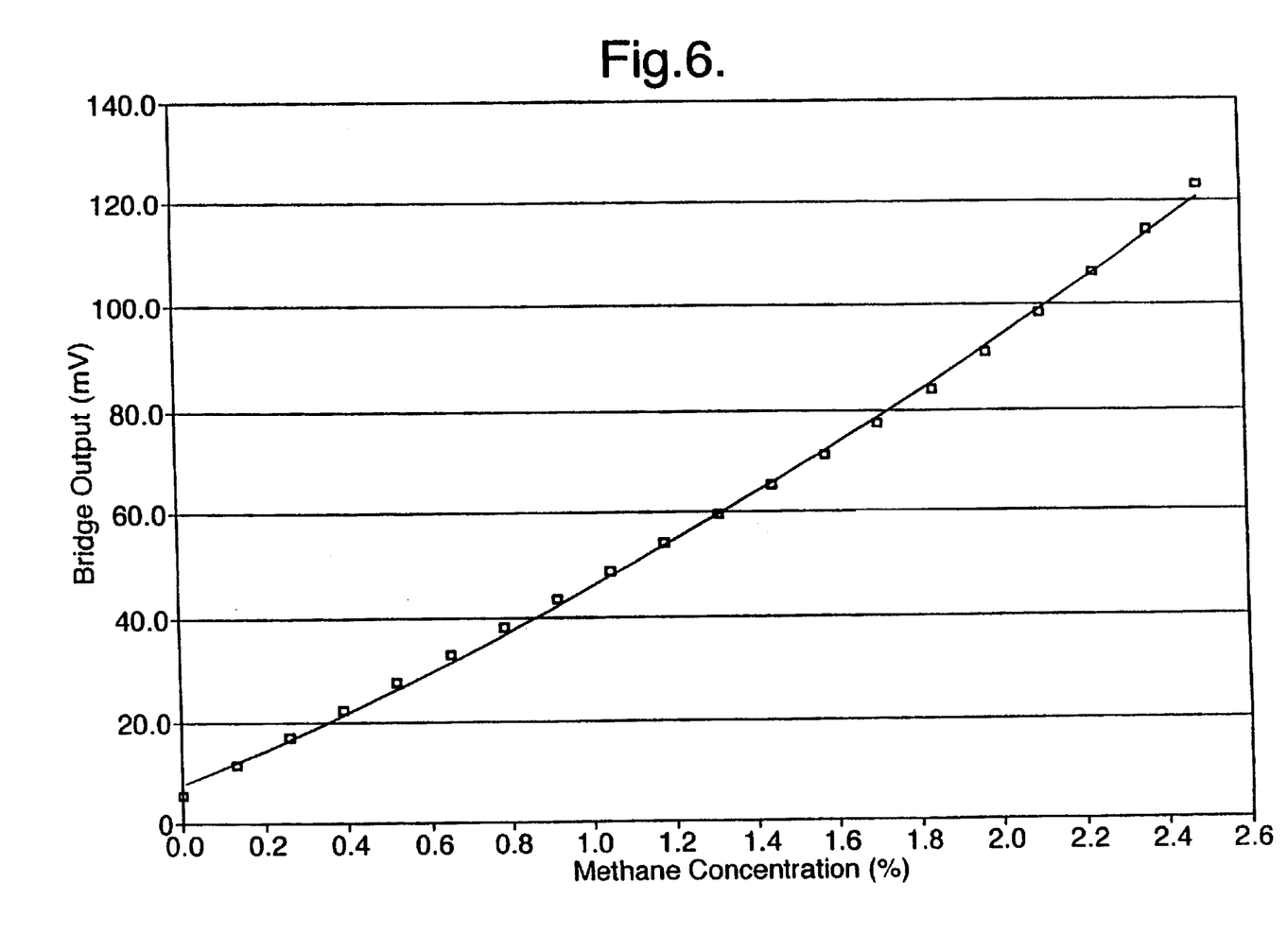
FIG. 6 illustrates the variation of mean bridge output with methane concentration.

FIG. 6 shows results obtained in a test to examine the response of a mesoporous Pd device (20 mC deposition, operated at 5.5V) to a series of increasing methane concentrations of up to 2.5% (averaged over about 2.5 mins at each concentration). From FIG. 6 it is clear that the bridge output is a near-linear function of concentration even in the absence of a diffusion limiting housing around the sensor. The graph shows a second-order regression line fitted to the experimental data for illustrative purposes only.

Figure 7:
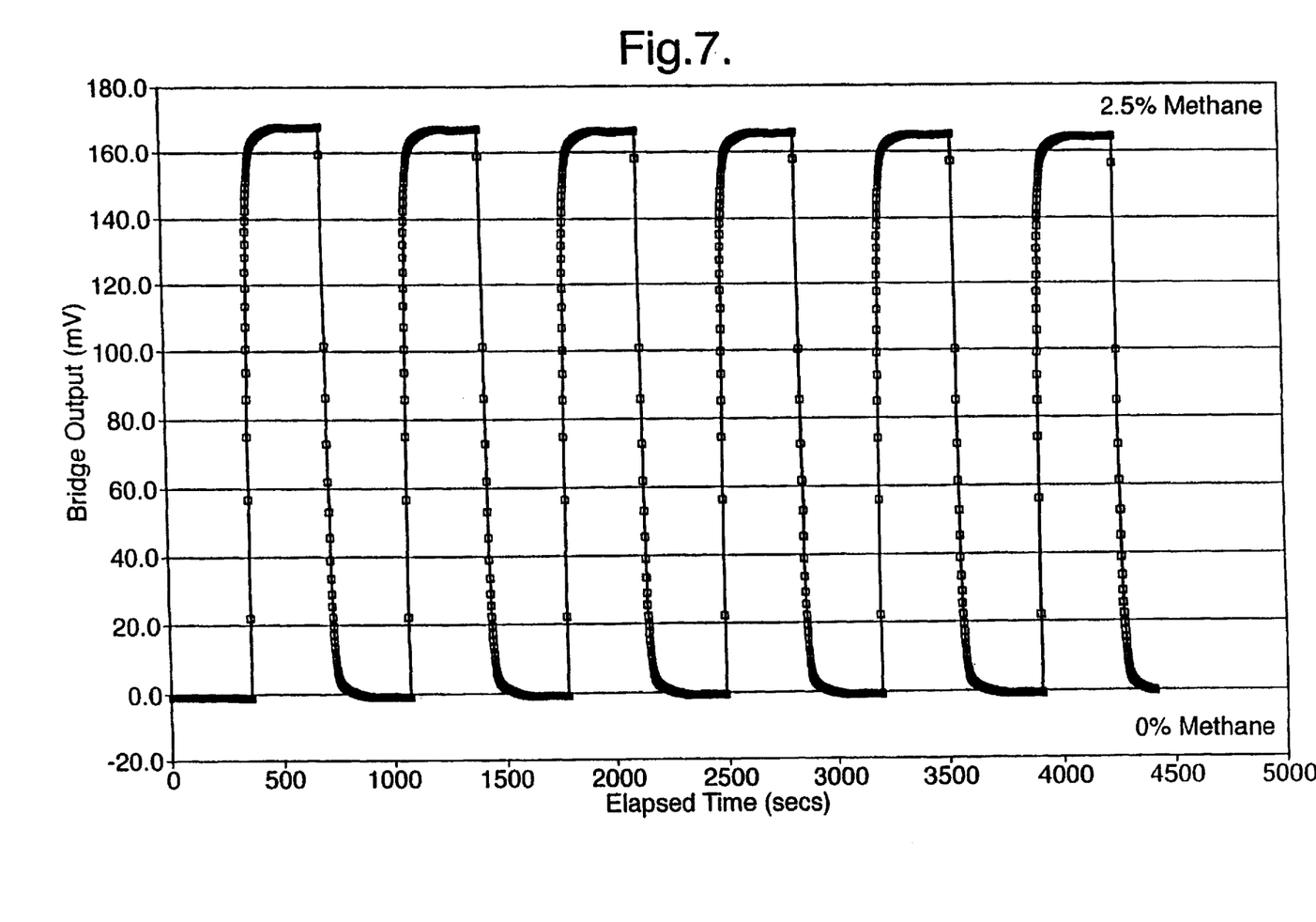
FIG. 7 illustrates the variation of bridge output with time during repeated exposures to 0% and 2.5% methane in air.
Figure 8:
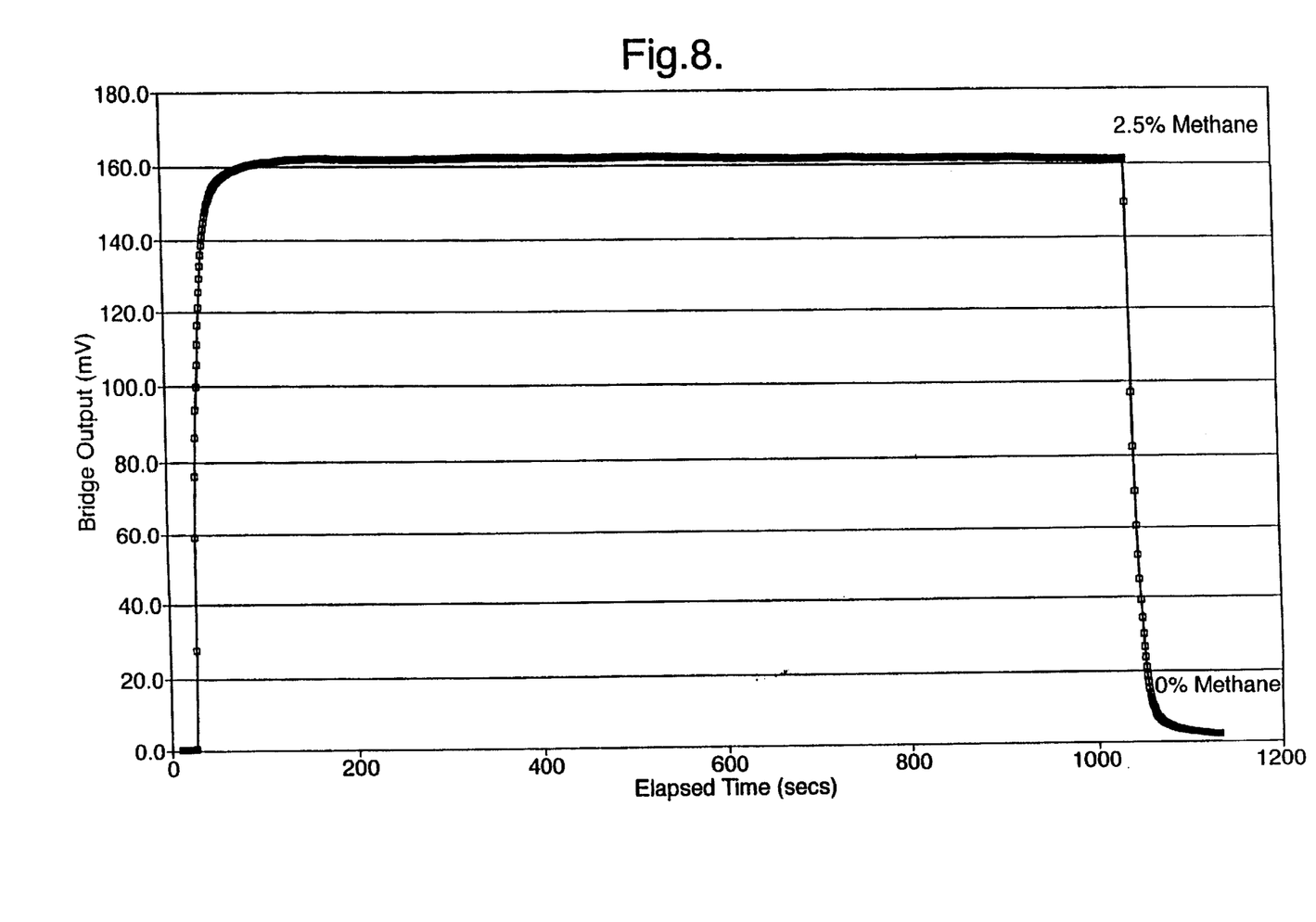
FIG. 8 illustrates the variation of bridge output with time during extended exposure to 2.5% methane in air.
Figure 9:
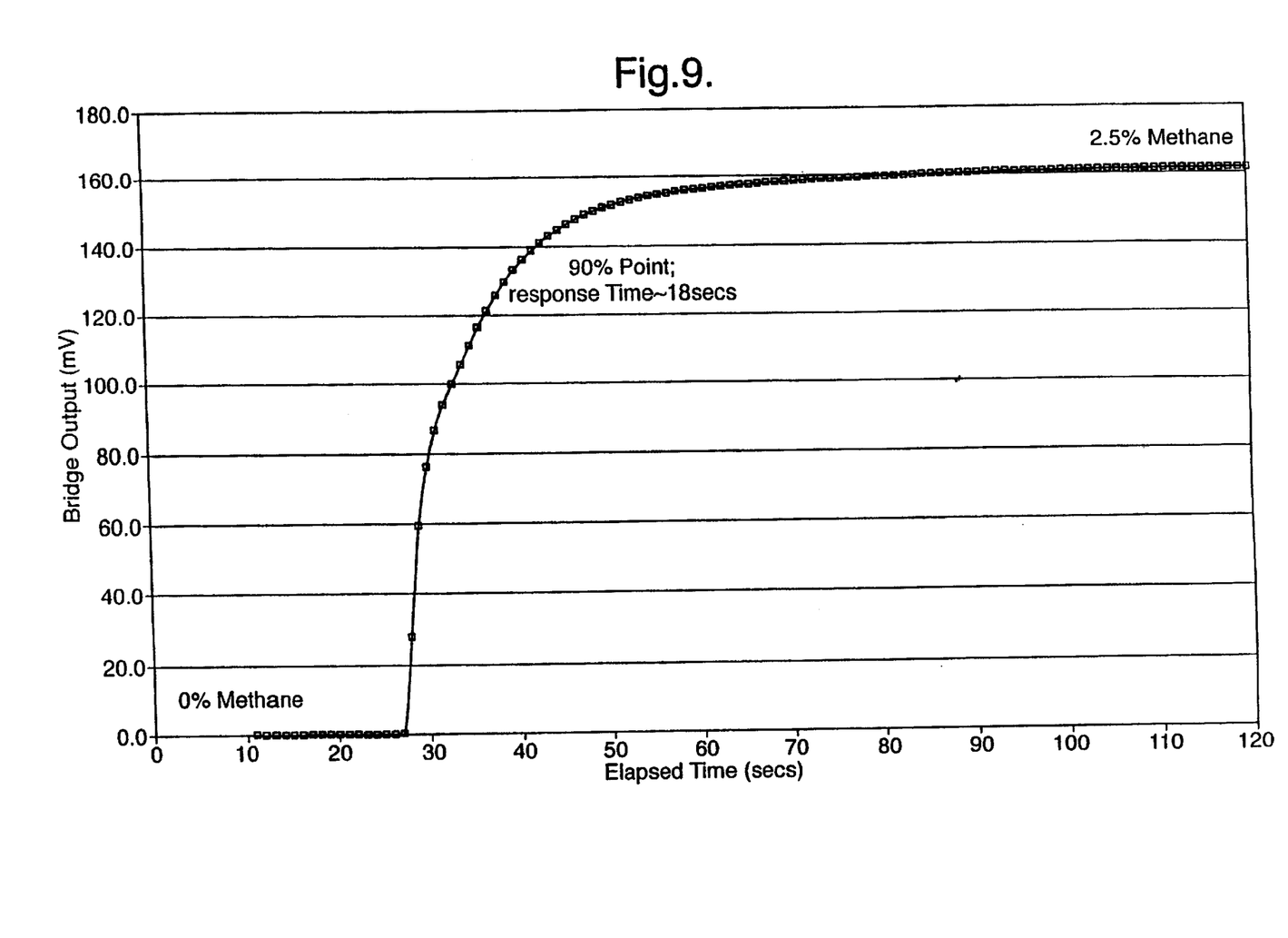
FIG. 9 illustrates the initial portion of FIG. 8 in enlarged detail.

FIG. 7 indicates that a mesoporous Pd device (20 mC deposition, operated at 5.5V) subjected to repeated exposures to air and 2.5% methane exhibits good reproducibility of response over 6 cycles, and recovers to the original baseline quite reliably in each case. In a longer exposure to the same methane concentration (FIG. 8), the output stability was again found to be quite acceptable, with good recovery back to the original air baseline. Finally, FIG. 9 shows the early stages of this test in more detail and indicates that, even without allowing for the dead volume inherent in the experimental system, acceptable response times ($T_{90}$=18 secs) are obtained.

In summary, it has been shown that the micromachined devices are capable of producing a stable, fast and reproducible response to methane, with a stable zero gas baseline.

The sensitivity and power consumption of (a) the experimental mesoporous devices, (b) conventional low power coil elements and (c) a planar device known as the Microsens Catalytic Gas Sensor MCGS-2101 made by Microsens S.A. have been tabulated below:

| Parameter | Experimntal Device | Conventional Coil | Microsens Planar Device |
|---|---|---|---|
| Sensitivity (mV/% methane) | 60 | 40 | 24 |
| Power Consumption (mW per element) | 165 | 125 | 30 |

Figure 10:
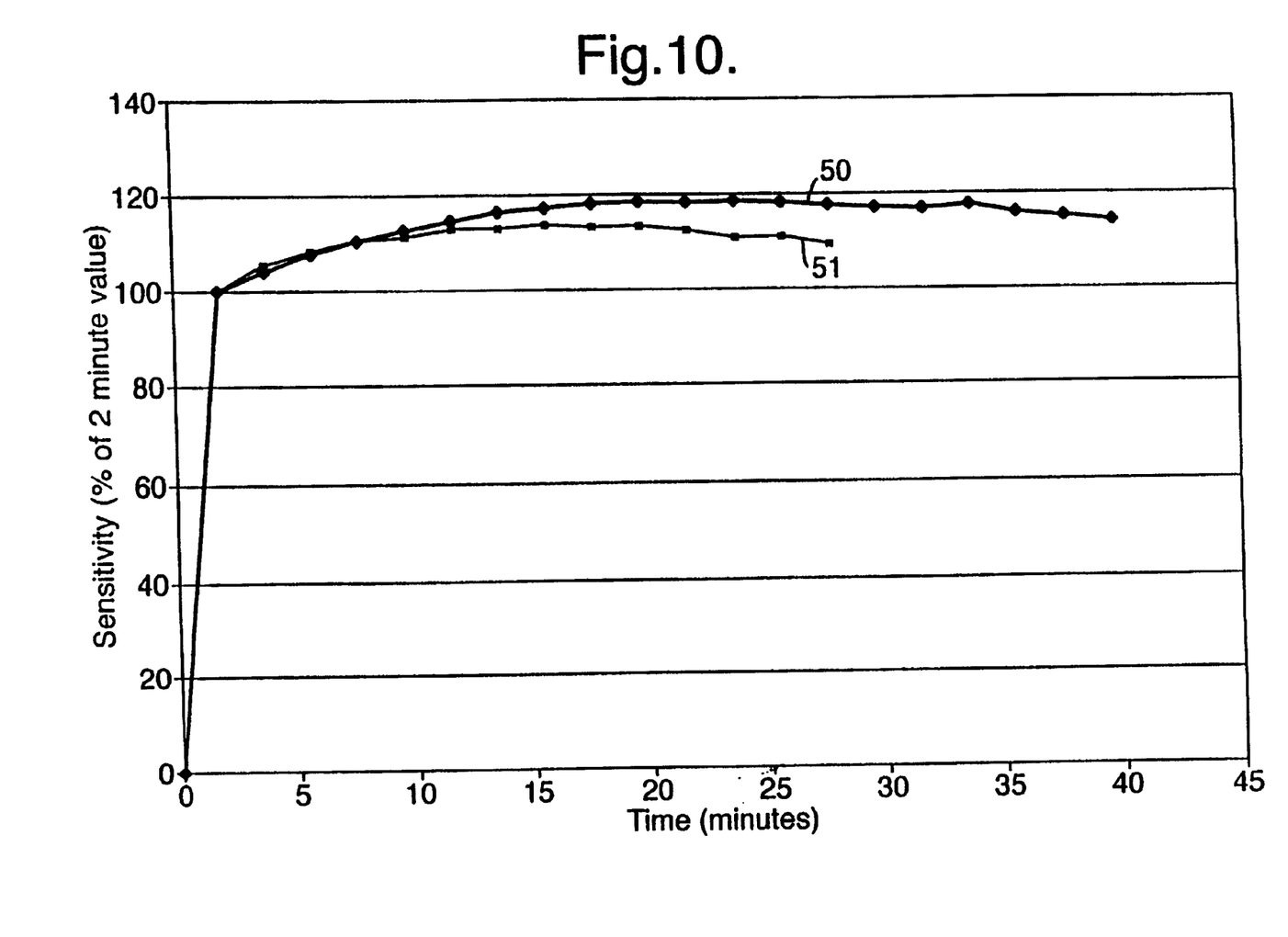
FIG. 10 illustrates the poison resistance of the pellistor.

The effect of a well known pellistor poison has been shown to have minimal effect upon the sensitivity behaviour of the new devices. FIG. 10 compares the relative sensitivities to 2.5% methane in air (with 100 ppm hydrogen sulphide 50 and without hydrogen sulphide 51) of two planar devices coated in the mesoporous Pd catalyst. The results confirm that, as is the case for the best current commercial wirewound pellistors, the presence of the $H_2S$ has negligible effect upon the methane sensitivity over periods of many minutes.

What is claimed is:

1. A method of manufacturing a pellistor, the method comprising providing a porous catalyst layer on a heater by electrodepositing material from a mixture containing the catalyst and a structure-directing agent in an amount sufficient to form an homogenous lyotropic liquid crystalline phase in the mixture.

2. A method according to claim 1, further comprising removing the structure-directing agent after the material has been deposited.

3. A method according to claim 2, wherein the structure-directing agent comprises an amphiphilic organic compound or compounds.

4. A method according to claim 3, wherein the structure-directing agent comprises octaethylene glycol monohexadecyl ether.

5. A method according to claim 1, wherein the catalyst comprises one or more of palladium, platinum, iridium and rhodium.

6. A method according to claim 1, wherein the mixture further comprises a solvent.

7. A method according to claim 1, wherein the heater comprises a planar electrode provided on a substrate.

8. A method according to claim 7, wherein the heater has a serpentine form.

9. A method according to claim 8, wherein the substrate comprises a micro machined membrane.

10. A method according to claim 9, wherein the material is deposited onto the heater through a mask.

11. A method according to claim 9, wherein the material forms a catalyst layer covering an area less than 100 $\mu m^2$.

12. A method according to claim 11, further comprising, prior to the electrodepositing step, providing an electrode on the heater structure which contacts the mixture during the electrodepositing process.

13. A method according to claim 12, wherein the electrode comprises gold.

14. A method according to claim 13, wherein the electrode is vapour deposited onto the heater structure.

* * * * *